(12) United States Patent
Balaban et al.

(10) Patent No.: US 8,198,433 B2
(45) Date of Patent: Jun. 12, 2012

(54) ACYLATED PHTHALOCYANINES

(75) Inventors: Teodor Silviu Balaban, Karlsruhe (DE); Mihaela Carmen Balaban, Karlsruhe (DE)

(73) Assignee: Karlsruher Institut Fuer Technologie, Karlsruhe (DE)

( * ) Notice: Subject to any disclaimer, the term of this patent is extended or adjusted under 35 U.S.C. 154(b) by 0 days.

(21) Appl. No.: 12/862,794

(22) Filed: Aug. 25, 2010

(65) Prior Publication Data
US 2011/0054166 A1 Mar. 3, 2011

(30) Foreign Application Priority Data
Aug. 26, 2009 (DE) .................. 10 2009 043 862

(51) Int. Cl.
*C07B 47/00* (2006.01)
*C07D 487/22* (2006.01)
(52) U.S. Cl. ........................................ 540/145
(58) Field of Classification Search .................. 540/145
See application file for complete search history.

(56) References Cited

U.S. PATENT DOCUMENTS 6,087,492 A * 7/2000 Wolleb ..................... 540/139

FOREIGN PATENT DOCUMENTS
DE 101 46 970 A1 4/2003

OTHER PUBLICATIONS

Zefirov et al., Catalysis by topologically anchored metal complexes Liquid-phase hydroxylation of benzene by H2O2 in the presence of zeolite-supported Fe(II) phthalocyanine. Canadian Journal of Chemistry (1998), 76(6), 955-959 Coden: CJCHAG; ISSN: 0008-4042.*
Dennis Mössinger, Dissertation: "Stereoselective Reductions with Borane Reagents", Chapter 3, pp. 32-47 (English Translation), (2003).

* cited by examiner

*Primary Examiner* — Paul V. Ward
(74) *Attorney, Agent, or Firm* — Norman B. Thot

(57) ABSTRACT

An acylated phthalocyanine of the formula:

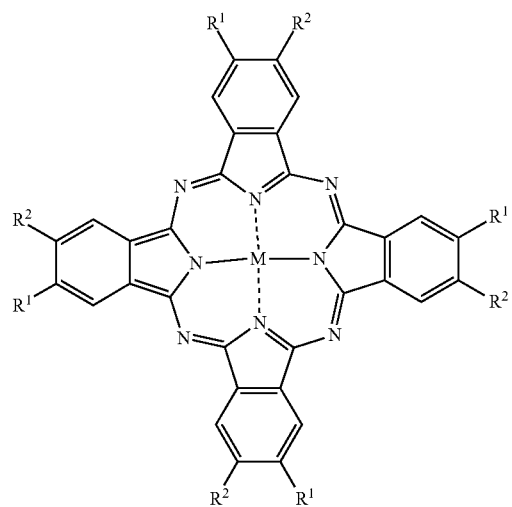

wherein,
$R^1$ and $R^2$ are each selected from the group consisting of hydrogen, alkyl, alkoxy and acyl radicals of the formulae —COR and —CRHOH,
whereby 1-4 of the 8 $R^1$ and $R^2$ radicals are selected from the group consisting of —COR and —CRHOH, and if $R^1$ or $R^2$ on a benzene ring is selected from —COR or —CRHOH, then the other respective $R^1$ or $R^2$ radical on the benzene ring is hydrogen,
R is $CH_3(CH_2)_n$— where n is 0-15,
M is at least one of Mg, Zn, Cd, Cu, Ni, Co, Fe, Pt, Pd or Sn,
alkyl is $C_nH_{2n+1}$ where n is 7-14, and
alkoxy is $OC_nH_{2n+1}$ where n is 6-15.

9 Claims, 1 Drawing Sheet

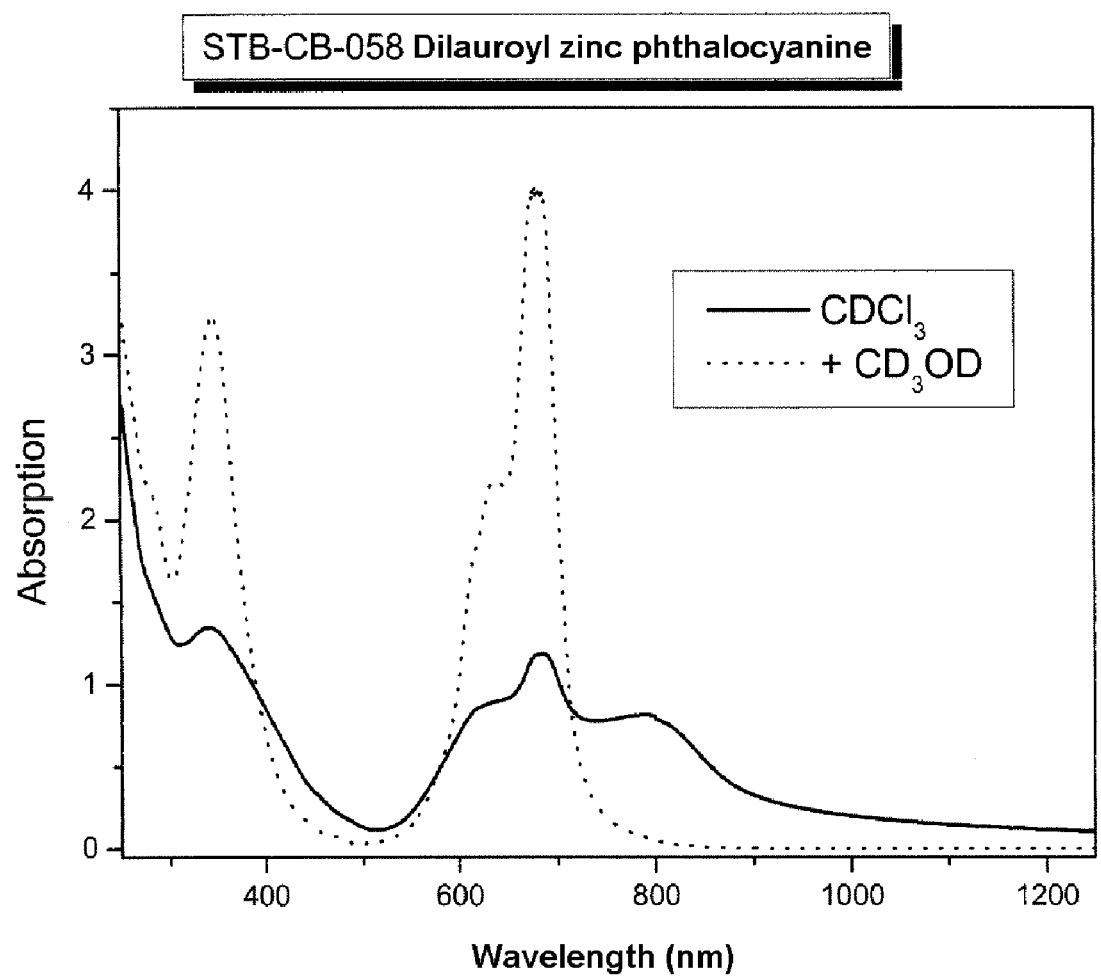

ACYLATED PHTHALOCYANINES

CROSS REFERENCE TO PRIOR APPLICATIONS

Priority is claimed to German Patent Application No. DE 10 2009 043 862.9, filed Aug. 26, 2009. The entire disclosure of said application is incorporated by reference herein.

FIELD

The present invention relates to specific phthalocyanines, to processes for their preparation and to uses thereof.

BACKGROUND

Natural photosynthesis has mastered photon capture under very weak illumination, for example at 100 m below sea level. The natural chromophores used for this cannot be reproduced in the laboratory, and are very fragile and difficult to handle.

Light has been collected efficiently in nature itself for at least 2.5 billion years. To date, similar achievements have been made only by the building of large light-collecting antennas or by self-assembly of fully synthetic molecules, for example, as described in DE 101 46 970 A1, which is incorporated by reference herein.

Phthalocyanines are stable dyes which have good pigment properties, for example, high absorption coefficients in the visible range. Attempts to date to incorporate phthalocyanines into dye-sensitized solar cells have yielded only very low efficiency, for example, low power conversion of light to electrical current. A problem may lie in the tendency of the dyes to aggregate, which leads to quenching of the fluorescence. Therefore, phthalocyanines typically result only in a radiationless deactivation process.

Conventional silicon-based solar cells, even though they exhibit good efficiency owing to the complex purification processes, are too expensive to build large-area systems. Dye-sensitized solar cells, in contrast, exhibit a significantly lower efficiency, but are producible with low production costs.

SUMMARY

An aspect of the present invention is to provide for efficient light collection by means of artificial molecules.

Proceeding from the model of the bacteriochlorophylls, and through experiences with self-assembling porphyrins, an aspect of the present invention was to provide molecules, for example, phthalocyanines, which have recognition groups that enable self-assembly and have solubility-promoting groups, without increasing complexity, so that the production costs remain low.

Another, alternative aspect of the present invention, was to provide a process for producing the molecules which is uncomplicated to realize.

Another, alternative aspect of the present invention, was to provide environmentally-friendly solar power generation and conversion of light energy.

In an embodiment, the present invention provides acylated phthalocyanines of the formula:

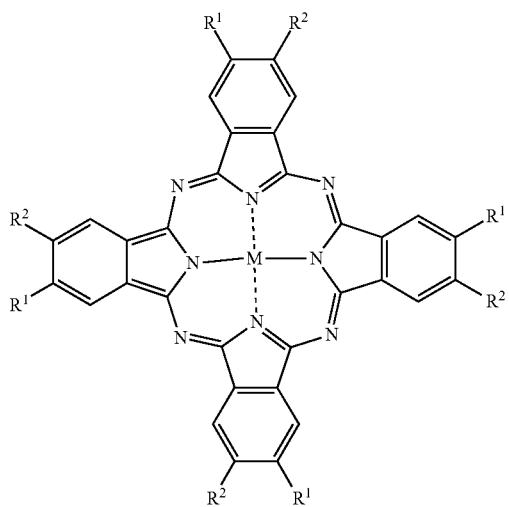

wherein, $R^1$ and $R^2$ are each selected from the group consisting of hydrogen, alkyl, alkoxy and acyl radicals of the formulae —COR and —CRHOH, whereby 1-4 of the 8 $R^1$ and $R^2$ radicals are selected from the group consisting of —COR and —CRHOH, and if $R^1$ or $R^2$ on a benzene ring is selected from —COR or —CRHOH, then the other respective $R^1$ or $R^2$ radical on the benzene ring is hydrogen, R is $CH_3(CH_2)_n$— where n is 0-15, M is at least one of Mg, Zn, Cd, Cu, Ni, Co, Fe, Pt, Pd or Sn, alkyl is $C_nH_{2n+1}$ where n is 7-14, and alkoxy is $OC_nH_{2n+1}$ where n is 6-15.

BRIEF DESCRIPTION OF THE FIGURE

The present invention is described in greater detail below on the basis of embodiments and of the FIGURE in which:

FIG. 1 shows the absorption of a dilauroyl-zinc-phthalocyanin across various wavelengths as measured in two different solvents.

DETAILED DESCRIPTION

In the context of the present invention, all amounts, unless stated otherwise, are understood to mean weights.

In the context of the present invention, the term "room temperature" means a temperature of 20° C. Temperatures are, unless stated otherwise, in degrees Celsius (° C.).

Unless stated otherwise, the reactions and process steps cited are performed at standard pressure/atmospheric pressure, i.e., at 1013 mbar.

In the context of the present invention, "solubility" is understood to mean the amount of a substance which can just be dissolved in a particular amount of a particular solvent at a particular temperature. In the present invention, solubility is reported in g/l, for a particular solvent and for a temperature of 20° C. Substances with good solubility in the context of the present invention are understood to mean those with a solubility of 3 to 10 g/l, and sparingly soluble substances to mean those having a solubility of less than 0.1 g/l.

In the context of the present invention, phthalocyanines of the general formula

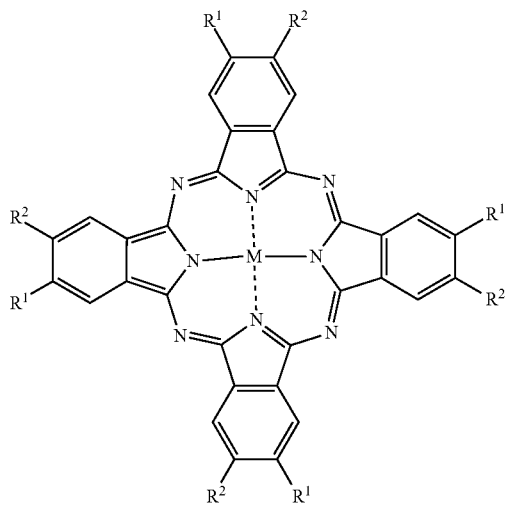

have been found, in which $R^1$ and $R^2$ are each selected from the group consisting of hydrogen, alkyl, alkoxy, acyl radicals of the formulae —COR and —CRHOH, with the proviso that not less than one and not more than four of the eight radicals are selected from the group consisting of —COR and —CRHOH, and with the proviso that, if $R^1$ or $R^2$ on one benzene ring is selected from —COR and —CRHOH, the other $R^1$ or $R^2$ radical on this benzene ring is hydrogen, where R is $CH_3(CH_2)_n$— where n=0-15, for example, n=5-15, M is selected from the group consisting of Mg, Zn, Cd, Cu, Ni, Co, Fe, Pt, Pd, Sn and mixtures thereof, for example selected from the group consisting of Mg, Zn, Cd, Cu, Ni and mixtures thereof, alkyl is $C_nH_{2n+1}$ where n=7-14, and alkoxy is $OC_nH_{2n+1}$ where n=6-15.

In an embodiment of the present invention, the phthalocyanine is diacylated and n in each case is from 5 to 15.

In an embodiment of the present invention, the R radicals are, for example, $CH_3(CH_2)_5$— and/or $CH_3(CH_2)_{11}$—.

In an embodiment of the present invention, n=7-15.

Attempts to derivatize unsubstituted phthalocyanines by the well-known Friedel-Crafts acylation have to date not been successful. The present invention therefore also provides a process for preparing acylated phthalocyanines.

In order to provide a highly ordered supramolecular arrangement of the chromophores, the recognition groups should only be present in particular positions.

In an embodiment of the present invention, an extended synthesis route has been provided which proceeds via several stages.

In an embodiment of the present invention, the following synthesis method can be used to provide the recognition groups only in particular positions:

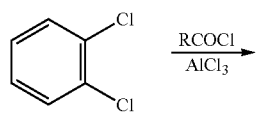

R = $CH_3(CH_2)_n$-
n = 0-15

In the last stage of the aforementioned synthesis, the introduction of a protecting group is optional and can be employed only when strong bases (such as alkali metal alkoxides) are used in the subsequent process. For example, it is not necessary for DBU.

A reason why no acyl phthalocyanines have been described in the literature can be that the condensation conditions which serve to form the macrocycle are in principle incompatible with a reactive carbonyl group. In the context of the present invention, it has surprisingly been found how the carbonyl group can be protected while at the same time being able to attach the protecting group in good yields and remove it again after the desired condensation to provide the phthalocyanine.

In an embodiment, the synthesis method of the present invention provides for the Friedel-Crafts acylation of ortho-dichlorobenzene with acyl radicals $R=C_nH_{2n+1}$ where n>6. Such 4-acyl-1,2-dichlorobenzenes have not to date been described. This is probably attributable to the low reactivity, which, however, was overcome in the context of the present invention by high temperatures, especially between 100° C. and 120° C., longer reaction times of 5 hours and more, and active aluminium chloride (active $AlCl_3$ herein means new or anhydrous $AlCl_3$) as a Friedel-Crafts acylation reagent/catalyst.

In an embodiment, the synthesis method of the present invention provides for the palladium-catalysed dicyanation of 4-acyl-1,2-dichlorobenzene derivatives. Phthalodinitriles serve as a base unit in the phthalocyanine synthesis of the present invention. Palladium catalysis is compatible with acyl groups, and so no protecting groups are needed in this case. For this reaction, the Pd catalyst is prepared in situ from the Pd complex (tris(dibenzylideneacetone)dipalladium(0)) and ferrocene (1,1'-bis(diphenylphosphino)ferrocene). If desired, it is possible to add active zinc (treated with HCl before the reaction). The reaction is performed at temperatures of 80 to 160° C., for example, 100 to 140° C., or 130 to 150° C., over the course of 2 to 8 hours, for example, 3 to 5 hours, or 3.5 to 4.5 hours.

In an embodiment, the synthesis method of the present invention does not attack an acyl group. Additional stages associated with the protecting groups can therefore be avoided.

The 4-acyl-1,2-dichlorobenzenes, the 4-acylphthalodinitriles and the acetals thereof, where the acyl radical in each case has an alkyl chain $CH_3(CH_2)_n$ where n=7-15, are intermediates in the process according to the present invention, but are additionally novel compounds per se. They are suitable for the phthalocyanine syntheses, for example, in the process according to the present invention detailed above. Specific examples include 4-acyl-1,2-dichlorobenzene, 4-acylphthalodinitrile, and 4-(5,5-dimethyl-1,3-dioxane)phthalodinitrile, wherein each respective compound has an acyl radical with an alkyl chain, $CH_3(CH_2)_n$, where n is 7-15.

Given 4-substitution, in the condensation of the 4-acylphthalodinitriles, the four isomers expected overall are set forth below.

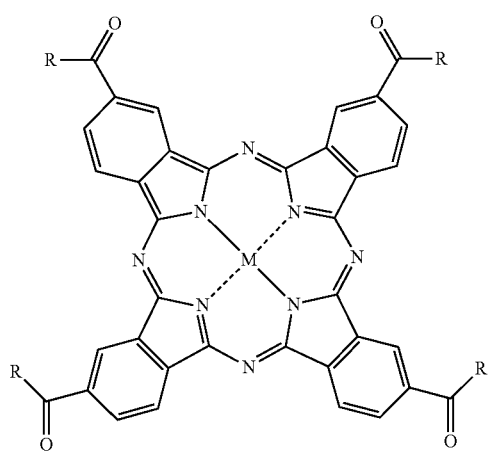

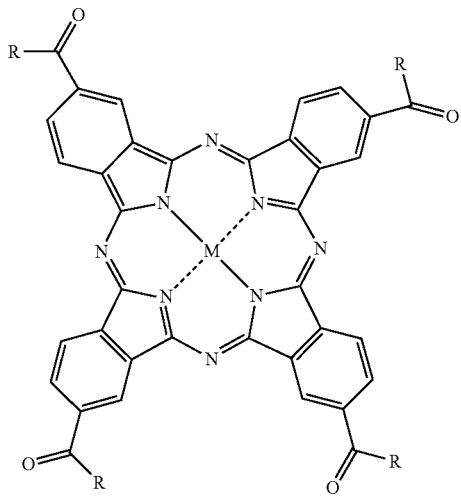

-continued

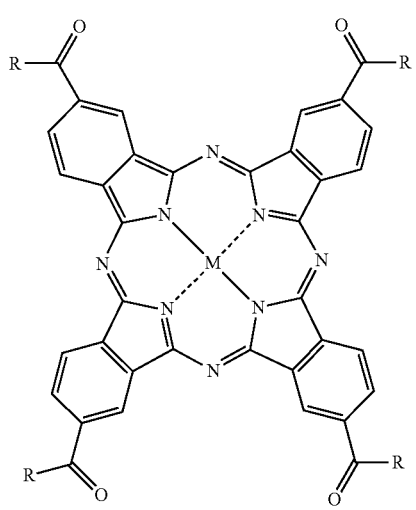

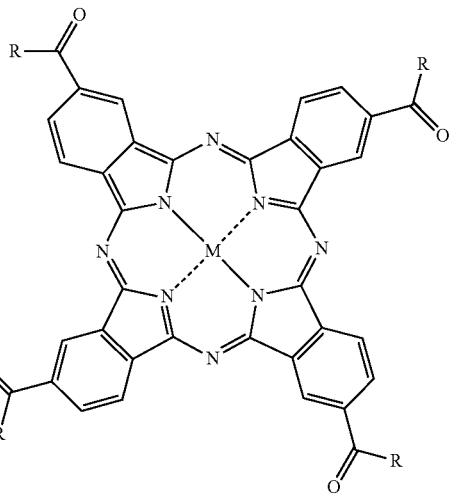

In an embodiment of the present invention, a mixed condensation with a second phthalonitrile, which may be either mono- or disubstituted, is provided

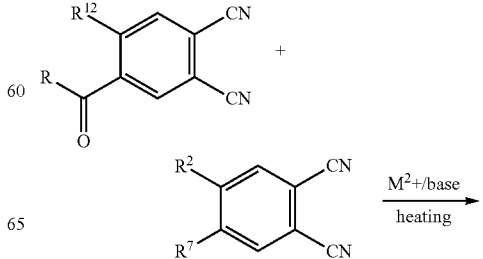

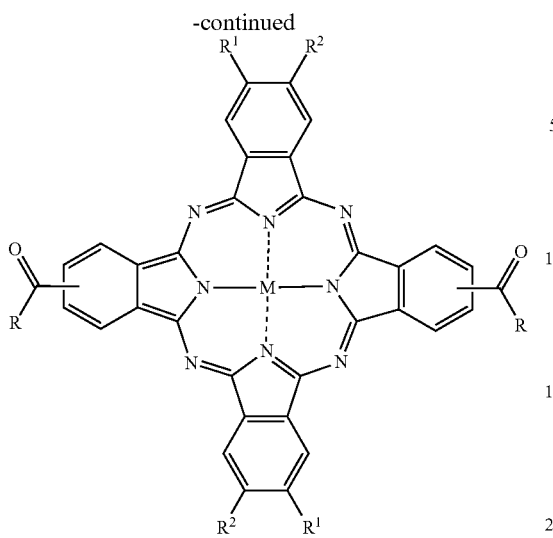

wherein
$R^{1,2}$=hydrogen,
$R^1$, $R^2$, alkyl and M are as described above,
wherein a mixture of non-, mono-, di-, tri- and the four tetraacylated isomers of the above diagram is obtained.

The bases used in the context of the present invention may be a wide variety of commonly used bases, including alkali metal alkoxides, for example, lithium pentoxide, sodium ethoxide, sodium isopropoxide. In an embodiment of the present invention, non-nucleophilic bases selected from the group consisting of 1,8-diazabicyclo[5.4.0]undec-7-ene (DBU), pyridine, quinoline, 2,6-di-tert-butylpyridine and mixtures thereof can be used. In an embodiment of the present invention, DBU can be used as the base.

No acyl groups occur in the alpha position, as a result of which the isomer mixture is less complex overall and HPLC can be used to separate and obtain the desired phthalocyanines, for example, diacylphthalocyanines.

The diacylphthalocyanines exhibit a tendency to self-assemble. This is evident by virtue of broad and red-shifted absorption spectra as shown in FIG. 1.

In the context of the present invention, it has surprisingly been found that self-arrangement occurs even in solvents of moderate polarity, such as dichloromethane or chloroform.

This is not the case for porphyrin analogues known from the prior art, which exhibit self-arrangement in nonpolar solvents at best, such as n-hexane, cyclohexane or n-heptane.

In an embodiment of the present invention, it is possible to combine a recognition group (corresponding to R in the formulae) and solubility-promoting group (corresponding to the —CO— or —COH— group in the formulae) in one radical as a result of which the introduction thereof has been made possible.

By adding small amounts of solvents which coordinate the central metal atom, including alcohols such as, for example, methanol or ethanol, or pyridine, the assemblies can be decomposed again to monomers.

This is reflected in the absorption spectra with narrow, intense bands in the visible region (~680 nm) in FIG. 1.

This property can be utilized in order to match existing assemblies to a different purpose, or to correct incorrect assemblies by first decomposing them by addition of solvent and then subjecting them again to self-assembly by controlled removal or replacement of the solvent.

In an embodiment of the present invention, the central metal atom used for solar cells may, for example, be zinc or magnesium since the good fluorescence properties are maintained with high quantum yields. Other divalent metals can also be utilized, however, the heavy atom effect may result in quenching of fluorescence. Other possible applications may, however, exist where these other divalent metals are advantageous.

Further compounds of the present invention which have a high self-assembly tendency are the monoreduced compounds of the general formula

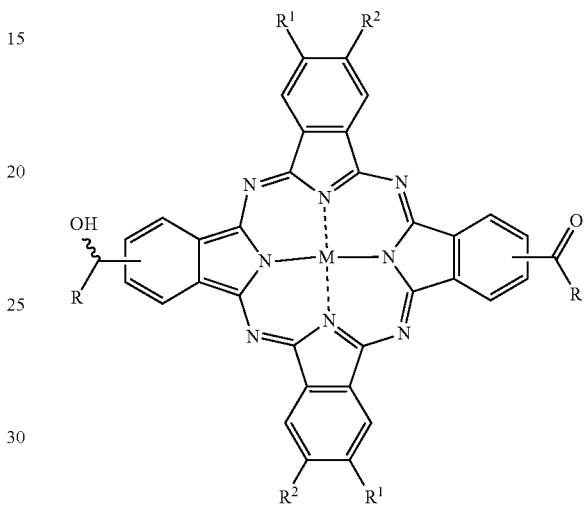

where the —COR or —CRHOH radicals may each be at the 3 or 4 position of the ring. These can be prepared in high yields from the diacylphthalocyanines where the variables are as defined above.

In an embodiment of the present invention, the monoreduction can be performed with sodium borohydride in methanol/dichloromethane which leads to an enantiomer mixture.

In an embodiment of the present invention, the monoreduction can be performed stereoselectively with chiral borohydrides, as described in the Diplom thesis by Dennis Mössinger "Stereoselektive Monoreduktionen an diacetyl-substituierten Porphyrinen" [Stereoselective Monoreductions on Diacetyl-Substituted Porphyrins] in Chapter 3, pages 32 to 47, which is incorporated by reference herein.

The acylated phthalocyanines show for the first time that broad absorption spectra in the wavelength range of 600-950 nm arise through self-assembly.

The acylated phthalocyanines of the present invention enable synthetic light collection and environmentally friendly efficacy over a wide area.

The acylated phthalocyanines of the present invention are soluble in polar solvents, for example, in slightly polar halogenated hydrocarbons such as dichloromethane and chloroform, for example to an extent of 3-10 g/l, and can be used as dyes, especially where the conventional phthalocyanines fail, for example, in chromatographic separation or purification, in mixtures in polymers and resins. Phthalocyanines are known as pigments in automotive finishes or in colour photocopiers, and have displaced other pigments by virtue of their brightness and stability. The phthalocyanines of the present invention are outstandingly suitable for this use too.

The phthalocyanines of the present invention exhibit the property of self-assembly to give large, well-ordered nanostructures. At the same time, the fluorescence properties are not lost. Also advantageous is the elevated solubility of 3-10 g/l of the phthalocyanines of the present invention compared to unsubstituted phthalocyanines which are insoluble in any solvent.

The elevated solubility of the phthalocyanines of the present invention also enables a wet-chemical preparation process for self-assembled structures. The phthalocyanines of the present invention are thereby dissolved in a polar solvent and added to a greater amount of a nonpolar and anhydrous solvent (since water can coordinate to the central metal ion and hence disrupt the assemblies), for example, hydrocarbons, which then spontaneously forms well-ordered assemblies.

An advantage of the phthalocyanine assemblies of the present invention is a greater absorption capacity compared to the monomers. A broad band extends up to 950 nm in the near infrared region, which constitutes a particular window for sunlight capture for solar cells. A further advantage of the assemblies of the present invention is an elevated quantum yield.

The phthalocyanines and assemblies thereof of the present invention can accordingly be used to produce dye-sensitized solar cells which have an increased efficiency compared to the prior art.

Uses of the phthalocyanines of the present invention include large-area hybrid solar cells which can also work efficiently under weak light conditions (for example in Germany).

Further uses of the phthalocyanines of the present invention is in the pigments industry including the cosmetics industry (green shades are, for example, most sought-after), or in medicine for photodynamic therapy (PDT).

In an embodiment of the present invention, the phthalocyanines can be used in light-sensitive layers, for example, in solar cells, as an active light-collecting layer, especially with phthalocyanines of the present invention arranged by self-assembly.

The phthalocyanines of the present invention can also be used in other applications.

In an embodiment, the present invention provides for assemblies comprising or consisting of acylated phthalocyanines of the present invention.

In an embodiment, the present invention provides for solar cells comprising the acylated phthalocyanines of the present invention.

The different configurations of the present invention can be combined with one another in any desired manner.

The present invention is now illustrated with reference to the following non-limiting examples.

EXAMPLES

Example 1

Preparation of 1,2-Dichloro-4-Lauroylbenzene

In a dry 250 ml three-neck flask with thermometer, reflux condenser (under nitrogen) and dropping funnel, 17.73 g of $AlCl_3$ (0.133 mol) were suspended in 50 ml of 1,2-dichlorobenzene and cooled to 0° C. While stirring vigorously, 31.6 ml of lauroyl chloride (0.133 mol) were slowly added dropwise (1 hour). The mixture was then allowed to cool until the temperature had reached room temperature. Subsequently, the mixture was heated gradually to approximately 100-105° C., in the course of which a change in colour was evident (from ochre to dark red). Subsequently, the mixture was stirred at this temperature for 5 hours and left to stand overnight at room temperature. To separate the complex, this mixture was cautiously poured onto 200 g of ice (5% HCl) while stirring. The mixture became a mustard-coloured paste which was extracted in ethyl acetate. The organic layer was then removed in a separating funnel and washed to neutrality with saturated sodium hydrogencarbonate solution (2×50 ml) and water. After drying over sodium sulphate, the ethyl acetate was evaporated off. The remaining 1,2-dichlorobenzene was distilled off under reduced pressure. The residue was chromatographed through a column (length=20 cm, diameter=5 cm) on silica gel (Merck 0.040-0.063 nm) with dichloromethane as the eluent.

This gave an oily substance with a boiling point (determined via Kugelrohr distillation) of 275° C. at 0.8 mbar.

Yield: 25.64 g, 87%

$^1$H NMR (300 MHz, $CDCl_3$) delta (ppm): 8.00 (d, J=2.1 Hz), 7.77 (d, J=2.1 Hz), 7.74 (d, J=2.1 Hz), 7.53 (d, J=2.4 Hz), 7.5 (d, J=2.4 Hz), 2.89 (m), 2.36 (m), 1.24 (m), 0.86 (m). $^{13}$C NMR (75 MHz, $CDCl_3$) delta (ppm): 198.08, 137.33, 136.51, 133.16, 130.61, 130.01, 127.03, 38.56, 31.86, 29.57, 29.44, 29.39, 29.29, 29.20, 24.05, 22.64, 14.08.

Example 2

Preparation of 1,2-Dichloro-4-Hexanoylbenzene

For the preparation of this compound, the procedure was as in Example 1. Instead of lauroyl chloride, however, 18.6 ml of hexanoyl chloride (0.13 mol) was used.

Yield: 15.02 g, 68.8%.

Example 3

Preparation of 1,2-Dicyano-4-Lauroylbenzene 1,2-Dichloro-4-lauroylbenzene (1 g, 3.04 mmol), tris(dibenzylideneacetone)-dipalladium(0) ($Pd_2(dba)_3$) (0.22 g, 0.12 mmol, 8 mol %), 1,1'-bis(diphenyl-phosphino)ferrocene (dppf) (0.26 g, 0.24 mmol, 16 mol %), active zinc (0.09 g, 0.72 mmol, 48 mol %) and zinc cyanide (0.57 g, 4.8 mmol, 160 mol %) were weighed under nitrogen and added in solid form to a dry 50 ml flask. 15 ml of N,N-dimethylacetamide (DMA) which had been purged with nitrogen for 5 minutes beforehand were injected via a septum cap. The reaction mixture was stirred at 120° C. under nitrogen for 4 hours. Thereafter, this reaction mixture was left to stand at room temperature overnight while stirring. Thereafter, the reaction mixture was transferred to a separating funnel, diluted with 100 ml of ethyl acetate, and washed with 50 ml of $NH_4OH$ (12.5% aq. $NH_3$) and saturated sodium chloride solution until the pH was neutral. The product was dried over sodium sulphate and the solvent was then vaporized on a rotary evaporator. This was followed by chromatography using a column (length=30 cm, diameter=3.5 cm) on silica gel (Merck 0.040-0.063 nm) with a mixture of ethyl acetate:hexane=1:2 (v/v) as the eluent.

Yield: 0.5 g, (53%)

$^1$H NMR (300 MHz, $CDCl_3$) delta (ppm): 8.34 (d, J=1.2 Hz), 8.27 (d, J=1.8 Hz), 8.25 (d, J=1.8 Hz), 7.95 (d, J=0.3 Hz), 7.92 (d, J=0.3 Hz), 2.98 (t), 2.37 (t), 1.25 (m), 0.87 (t).

Example 4

Preparation of Acylated Phthalocyanine

In a dry 250 ml three-neck flask with a thermometer, reflux condenser (under nitrogen), 0.5 g of 1,2-dicyano-4-lauroylbenzene (1.6 mmol), 0.2 g of phthalonitrile, 150 ml of 1-pentanol and 1.22 g of 1,8-diazabicyclo[5.4.0]undec-7-ene (8 mmol) were mixed. This reaction mixture was purged with nitrogen for 10 minutes. Thereafter, it was heated to 130° C., and 0.36 g of zinc acetate (2 mmol) was added. The mixture was heated further to reflux, and then the temperature was maintained for 48 hours. The colour changed to turquoise. The pentanol was distilled off under reduced pressure. The residue was dissolved in dichloromethane (150 ml), and washed with saturated ammonium chloride solution (2×50 ml), saturated sodium chloride solution (50 ml) and water (50 ml). The solvent was vaporized to leave a turquoise residue.

Example 5

Alternative Preparation of Acylated Phthalocyanine

The procedure was as in Example 4, with the following differences:

The reaction mixture was microwave-treated with a power of 150 mW at a temperature of 140° C. and a pressure of 73 mbar while stirring vigorously. This allowed the reaction time to be reduced from 48 hours to 5 minutes.

The present invention is not limited to embodiments described herein; reference should be had to the appended claims.

What is claimed is:

1. An acylated phthalocyanine of the formula:

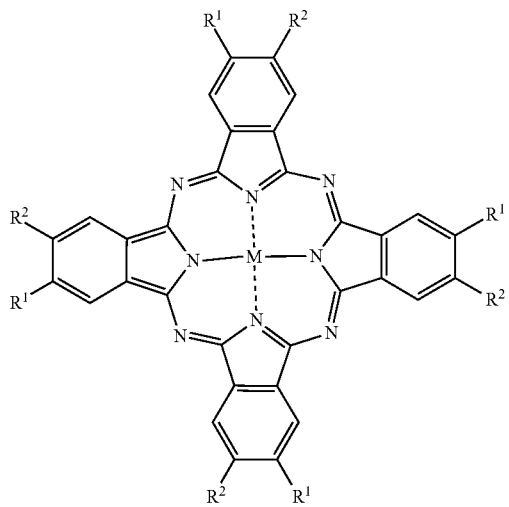

wherein,
  $R^1$ and $R^2$ are each selected from the group consisting of hydrogen, alkyl, alkoxy and acyl radicals of the formulae —COR and —CRHOH,
  whereby 1-4 of the 8 $R^1$ and $R^2$ radicals are selected from the group consisting of —COR and —CRHOH, and if $R^1$ or $R^2$ on a benzene ring is selected from —COR or —CRHOH, then the other respective $R^1$ or $R^2$ radical on the benzene ring is hydrogen,
  R is $CH_3(CH_2)_n$— where n is 0-15,
  M is at least one of Mg, Zn, Cd, Cu, Ni, Co, Fe, Pt, Pd or Sn,
  alkyl is $C_nH_{2n+1}$ where n is 7-14, and
  alkoxy is $OC_nH_{2n+1}$ where n is 6-15.

2. The compound as recited in claim 1, wherein the compound is monoacylated.

3. The compound as recited in claim 1, wherein the compound is polyacylated.

4. The polyacylated compound as recited in claim 3, wherein the polyacylated compound is at least one of diacylated, triacylated and tetraacylated.

5. The polyacylated compound as recited in claim 3, wherein R is $CH_3(CH_2)_n$— and n is 4, 10 or 14.

6. The polyacylated compound as recited in claim 5, wherein the polyacylated compound is diacylated.

7. The compound as recited in claim 1, wherein the compound comprises the formula:

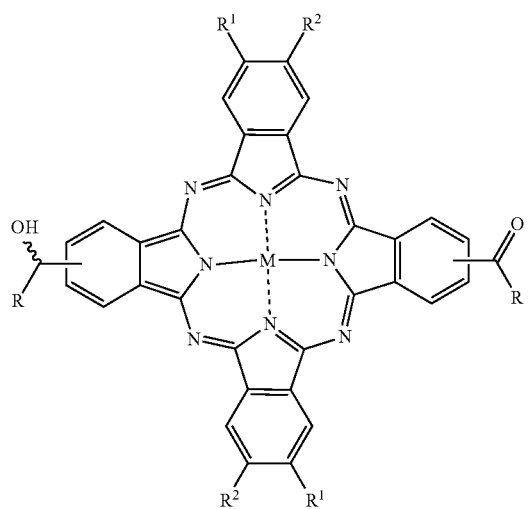

wherein the —COR or —CRHOH radicals are either at the 3 or 4 position of the respective ring.

8. Method of preparing an acylated phthalocyanine of the formula:

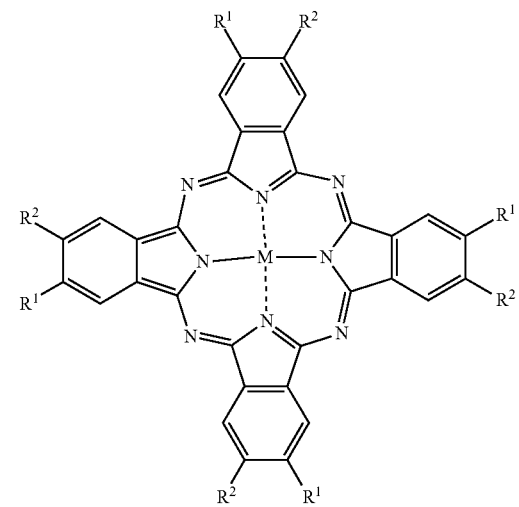

wherein,
  $R^1$ and $R^2$ are each selected from the group consisting of hydrogen, alkyl, alkoxy and acyl radicals of the formulae —COR and —CRHOH,
  whereby 1-4 of the 8 $R^1$ and $R^2$ radicals are selected from the group consisting of —COR and —CRHOH, and if $R^1$ or $R^2$ on a benzene ring is selected from —COR or —CRHOH, then the other respective $R^1$ or $R^2$ radical on the benzene ring is hydrogen, R is $CH_3(CH_2)_n$— where n is 0-15, M is at least one of Mg, Zn, Cd, Cu, Ni, Co, Fe, Pt, Pd or Sn, alkyl is $C_nH_{2n+1}$ where n is 7-14, and alkoxy is $OC_nH_{2n+1}$ where n is 6-15, the process comprising either:

condensing 4-acylphthalodinitriles with one another; or mixing a 4-acylphthalodinitrile of the formula:

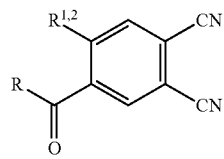

wherein, $R^{1,2}$ is hydrogen, and $R^1$, $R^2$ and alkyl are as above, with a 3,4-disubstituted phthalodinitrile having the formula:

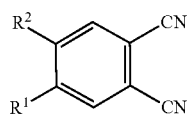

wherein, $R^{1,2}$ is hydrogen, and $R^1$, $R^2$ and alkyl are as above, with M, as above, at least one of an alkali metal alkoxide base and a non-nucleophilic base, while heating.

9. The method as recited in claim 8, wherein at least one of the phthalodinitriles and acetals are prepared by:

reacting 1,2-dichlorobenzene with $AlCl_3$ and RCOCl, wherein R is $CH_3(CH_2)_n$ and n is 0-15, to obtain a compound of formula 1:

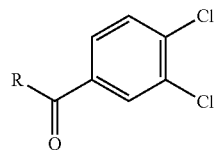

wherein R is $CH_3(CH_2)_n$ and n is 0-15;

reacting the compound of formula 1 with a palladium catalyst and zinc cyanide to obtain a compound of formula 2:

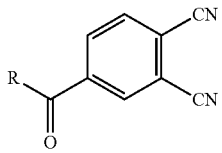

wherein R is $CH_3(CH_2)_n$ and n is 0-15; and reacting the compound of formula 2 with 3,3-dimethyl-1,5-pentadiol under acidic conditions to obtain a compound of formula 3:

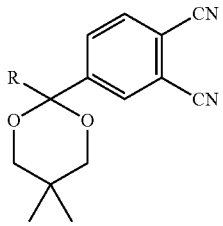

wherein R is $CH_3(CH_2)_n$ and n is 0-15.

* * * * *